United States Patent [19]
Franzen

[11] Patent Number: 5,770,860
[45] Date of Patent: Jun. 23, 1998

[54] METHOD FOR LOADING SAMPLE SUPPORTS FOR MASS SPECTROMETERS

[76] Inventor: Jochen Franzen, Helmer 17, D-28359 Bremen, Germany

[21] Appl. No.: 891,362

[22] Filed: Jul. 10, 1997

[30] Foreign Application Priority Data

Jul. 12, 1996 [DE] Germany .................. 196 28 178.4

[51] Int. Cl.$^6$ .................................................. H01J 49/00
[52] U.S. Cl. ........................................................ 250/288
[58] Field of Search ............................... 250/288, 288 A

[56] References Cited

U.S. PATENT DOCUMENTS

| | | | |
|---|---|---|---|
| 4,919,894 | 4/1990 | Daniel | 422/104 |
| 5,288,644 | 2/1994 | Beavis et al. | 436/94 |
| 5,498,545 | 3/1996 | Vestal | 250/288 |

FOREIGN PATENT DOCUMENTS 9603768  8/1996  WIPO .

Primary Examiner—Kiet T. Nguyen

[57] ABSTRACT

A method for rapid loading of large sample supports with a very large number of analyte samples for mass spectrometric analysis using the ionization method of matrix-assisted desorption by laser bombardment (MALDI). The method consists of using microtiter plates already introduced in biochemistry and molecular genetics for parallel processing of a large number of dissolved samples and a multiple pipette unit for simultaneous transfer of sample solution quantities from all reaction wells on a microtiter plate to the sample support, the sample support having at least the same size. By repeated loading with samples from other microtiter plates, spaced between the samples already applied, a very high density of samples can be achieved. Some of these samples can be reserved for a mass spectrometric determination of the sample positioning on the sample support, and the positions of the other samples can then be interpolated.

15 Claims, 1 Drawing Sheet

METHOD FOR LOADING SAMPLE SUPPORTS FOR MASS SPECTROMETERS

The invention concerns a method for rapid loading of large sample supports with a very large number of analyte samples for mass spectrometric analysis using the ionization method of matrix-assisted desorption by laser bombardment (MALDI).

The invention consists of using microtiter plates already introduced in biochemistry and molecular genetics for parallel processing of a large number of dissolved samples and a multiple pipette unit for simultaneous transfer of sample solution quantities from all reaction wells on a microtiter plate to the sample support, the sample support having at least the same size. By repeated loading with samples from other microtiter plates, spaced between the samples already applied, a very high density of samples can be achieved. Some of these samples can be reserved for a mass spectrometric determination of the sample positioning on the sample support, and the positions of the other samples can then be interpolated.

PRIOR ART

The ionization of biomolecular or polymer samples using matrix-assisted desorption by means of bombardment with short flashes from a pulsed laser has found wide acceptance in recent years and is used especially for time-of-flight mass spectrometers, but also in quadrupole RF ion traps or in ion cyclotron resonance spectrometers. This method is called "MALDI" (matrix-assisted laser desorption/ionization). This ionization method requires that samples applied to the surface of a sample support must be introduced into the vacuum system of the mass spectrometer. Prior art here is that a relatively large number of samples (about 10 to 100) are introduced together on a support, and the sample support is moved within the vacuum system in such a way that the required sample is situated specifically in the focus of the laser's lens system.

The analyte samples are placed on a sample support in the form of small drops of a solution, the drops drying very quickly and leaving a sample spot suitable for MALDI. Normally a matrix substance is added to the solution for the MALDI process and the sample substances are encased in the crystals when the matrix substance crystallizes while drying. However, other methods have also become known by which the sample substances are applied to a matrix layer which has been applied first and is already dry.

Current methods with visual control by the user via microscopic observation of the sample spots do not allow automation, but due to rapid progress in the MALDI technique, an automation of the sample ionization is emerging. Automation opens up the long demanded possibility for a processing of several tens of thousands of samples per day in mass spectrometer analysis. Parallel processing of large numbers of samples was introduced long ago in other areas of biochemistry and molecular genetics. For this goal, larger sample supports than used nowadays will be required, and a high densities of analyte samples on the sample support are demanded.

In biochemistry and molecular genetics, so-called microtiter plates have become established for parallel processing of many samples. The body size of these plates is 80 by 125 millimeters, with a usable surface of 72 by 108 millimeters. Today there are already commercially available sample processing systems which work with microtiter plates of this size. These originally contained 96 small exchangeable reaction vials in a 9 mm grid on a usable surface of 72 by 108 millimeters. Today, plates of the same size with 384 reaction wells imbedded solidly in plastic in a 4.5 mm grid have become standard. Plates with 864 reaction wells in a 3 mm grid are being discussed.

The parallel processing of high numbers of samples, for example in molecular genetics, consists not only in working with just one such microtiter plate, but rather in parallel working with a large number of such plates. For example, with simultaneous treatment of 120 such plates in a single PCR apparatus (PCR=polymerase chain reaction), more than 46,000 DNA segments could be multiplied a billion times simultaneously within a period of about 3 hours.

As yet, various sample supports with up to 30 millimeters diameter, in other systems up to 50 by 50 millimeters in size, are being used in commercial mass spectrometry. These appear too small for future requirements. Currently investigated trends indicate that tens of thousands of samples will be be analyzed daily if analyses can be automated.

Different types of sample supports can be used for automatic sample analyses. High numbers of smaller sample supports, for example, can be automatically fed to a mass spectrometer as described in U.S. Pat. No. 5,498,545. Such an automatic system is nevertheless complicated and it appears much more practical to locate tens of thousands of samples on a single sample support.

The number of samples on a sample support is mostly limited today by the long time required for loading of the samples on the support and by the perishability of the samples during this period of time. If about 40,000 analysis samples must be applied in sequence to a single sample support, and the application of each sample lasts only two seconds (although the transfer pipette can hardly be properly cleaned during this time), the entire loading process then lasts already more than 22 hours. For many MALDI methods, matrix substances are used which oxidize or hydrolize when exposed for long periods to wet air and thereby lose their effectiveness for the MALDI process. Also the biomolecular samples are often unstable, and sometimes must be stored cooled in solution and cannot be exposed for hours to laboratory air and heat.

Mass spectrometric analyses with parallel treatment of large numbers of samples are needed for genotyping, for determining individual gene mutations and for many other problems.

OBJECTIVE OF THE INVENTION

It is the objective of the invention to find a method with which appropriate sample supports can be loaded relatively quickly and safely with thousands of MALDI analyte samples, processed from initial samples in microtiter plates, so that they are accessible for automatic mass spectrometric analysis procedures.

DESCRIPTION OF THE INVENTION

It is the basic idea of the invention to adapt the sample support in its size and shape to microtiter plates, to preprepare it with a MALDI layer and to transfer all (for example 384) or at least a large subset of analyte samples from one microtiter plate onto the MALDI layer at the same time. Suitable for this transfer is the well-known multiple pipette unit which either has exactly as many pipettes as the microtiter plates has reaction wells, or at least a large subarray of pipettes. The array of micropipettes must possess the same spot spacing as the reaction wells on the microtiter plate, or an integer multiple thereof. When using microtiter plates with 384 analysis samples, preferredly all 384 samples may be transferred at the same time and placed in a sample spot array with 4.5 millimeter spot spacing on the MALDI layer. As an alternative, a multipipette with 96 pipette tips may be used, yielding a sample spot array with 9 millimeter spot spacing, but necessitating four sample transfers from one 384-well microtiter plate.

By cleaning the multipipettes, changing the microtiter plates and repeating this procedure, a second sample spot array with another 384 analysis samples from a second microtiter plate can be applied to the same sample support, whereby this sample spot array is just slightly offset (interlaced) from the first array. By repeating this procedure, 384 sample blocks (or, in the case of a 96-tip multipipette, 96 sample blocks) can be created on a sample support, while each sample point block contains a large number of sample spots each of which comes from a different microtiter plate.

For example, with a block of 5 by 5 sample spots and using a 384-well microtiterplate and a 384-tip pipette, a total of 5×5×384=9,600 samples can be applied while the sample spots can be spaced at a maximum of 0.9 millimeters from one another. The sample spots can each have a diameter of about 0.6 millimeters without problem. It is even possible to apply blocks of 11 by 11 sample spots with 400 micrometers of spacing and 300 micrometers diameter for each sample spot. This produces a total load of 46,464 samples on a single sample support plate. As shown below, even many more analysis samples can be applied.

The sample support can be provided with a lacquer layer of nitrocellulose, for example, as a preparation for the MALDI process, a suitable protonizing matrix component being added to the lacquer. Such coatings have been described in patent applications DE 19 617 011 and DE 19 618 032. This lacquer layer is extremely adsorptive for proteins and DNA. The molecules of the analyte substance are adsorbed very uniformly on the surface and thus allow automation of the MALDI ionization process. The lacquer layer partially decomposes during bombardment with laser light flashes in the focal area of the laser light, thus releasing the biomolecules without causing them to fragmentate. The hot gases from the explosion-like decomposition are cooled by adiabatic expansion in the surrounding vacuum so quickly that the large biomolecules are barely heated up. Ions from the added protonizing matrix component then react in the gas phase with the large biomolecules and cause their ionization. The biomolecules may also however be chemically pretreated so that they already carry a charge in a solid condition and thus are released mainly as ions. The analyte ions are then analyzed in the mass spectrometer, for example (as in the simplest case) for their molecular weight.

The multiple pipette unit contains the pipettes exactly in the spacing of the array of reaction wells on the microtiter plate (or in integer multiples of the distances). The pipettes can therefore reach into the reaction containers with spatial precision and synchronicity and take out the solution there. They can, for example, terminate in small steel capillaries of 200 micrometers in outside diameter which are arranged in conically pointed holders with extreme precision in the grid of the microtiter plates of 4.5 millimeters. With them, very precise sample spots of 200 micrometers diameter are produced on the MALDI layer of the sample support which are arranged exactly in the grid of the microtiter plate. The amount of sample in those spots is by far sufficient for a single mass spectrometric analysis. The pipettes can be designed as a large number of individual microliter syringes with synchronous movement of the plungers.

Much simpler however are passive pipettes which function rather like imprinting stamps. They may consist, for example, of small stainless steel wires of 200 micrometers diameter without an inner capillary aperture, again fitted into conically pointed holders. The very slightly hydrophilic pipette wires take up tiny droplets, very precisely dosed, from the sample solution which hang from the end of the wires, and apply them to the MALDI layer on the sample support using gravitation and capillary forces. The MALDI layer is slightly hydrophobic, therefore the drops do not spread out on the layer and can be dried to a sample spot of about 200 micrometers in diameter.

These passive pipette tips can be coated on the end with appropriate layers, for example with a layer which attracts the sample molecules to the surface and therefore removes them in greater concentrations from the sample solution. If the adsorptivity of this layer is less than that of the MALDI layer on the sample support, the sample molecules can again be preferentially deposited on the MALDI layer.

It is a further idea of the invention that positively or negatively charged analyte molecules in the solution are attracted via electrophoretic migration to the passive pipette wires and can be concentrated there in this way by supplying the pipette wires with an electrical voltage in relation to the microtiter containers. The counterelectrodes may be integrated into the walls of the containers (for example through semiconductive walls), however they may also be introduced separately from the multipipette unit by separate extra electrode tips. The droplets taken then contain considerably more analysis molecules than actually correspond to the concentration of analysis molecules in the solution found in the microtiter wells. Chemical decomposition of the sample molecules on the pipette wires can be avoided by a suitable coating. The sample molecules transported with the droplet onto the MALDI layer can be transferred to the MALDI layer by reversing the electrophoresis voltage.

These multiple pipette systems are moved by an automatic robot system in three axes. They have relatively long routes to cover and must therefore be able to move quite quickly. They must move at least from the microtiter plate to the sample support, from there to a wash and dry station and back again to a new microtiter plate. Due to these requirements, their positioning accuracy is limited, but at a reasonable cost, systems may be built which have a positioning accuracy of about 50 micrometers.

This positioning accuracy of present automated pipette handlers of about 100 micrometers already allows the above mentioned sample blocks of 11 by 11 sample spots with 400 micrometers sample spot grid and 200 micrometers sample spot diameter, however it is then necessary to check the position of the sample spots relative to each other by suitable methods inside the mass spectrometer. To do this, at least two sample blocks with suitable, easily ionizable reference substances are necessary which should be as far apart as possible. With these two sample blocks, the positions of the individual samples in regard to one another can be determined in the mass spectrometer by a thorough scanning procedure. From the positions of the sample points in two sample blocks, the positions of all other sample blocks can be interpolated, even if beside the parallel offset there should be an angular offset.

It is therefore a further idea of the invention to provide at least two sample blocks with suitable samples for the measurement of the positioning of the samples inside the blocks. It would be best if these sample blocks were provided with samples of known substances with high ionization yield in order to ease scanning. For security reasons, it is practical to provide not only two but four blocks for this and to use the blocks in the four corners of a sample support. 380 sample blocks still remain for the analyses of unknown substances.

A further aspect concerns quality control. It has to be secured that the correct sample spot on the carrier plate is being analysed, and the best alignment of the mass spectrometer has to be checked in relatively short time intervals. It is therefore a further reference substance in known concentration and thus have a control for correct mass measurement and correct overall sensitivity of the apparatus. When using the four corner blocks for position calibration, and one sample each from every 11×11 block for mass and sensitivity control, there are still 45,600 analyte samples remaining. The following table provides an overview of the number of utilizable analysis samples relative to the block size, if 384-well microtiter plates and 384-tip multipipettes are used:

| Samples per block (number of microtiter plates) | Maximum spacing (center to center) | Number of utilizable analyte samples |
| --- | --- | --- |
| 2 × 2 = 4 | 2,00 mm | 1 140 |
| 3 × 3 = 9 | 1,50 mm | 3 040 |
| 4 × 4 = 16 | 1,12 mm | 5 700 |
| 5 × 5 = 25 | 0,90 mm | 9 120 |
| 6 × 6 = 36 | 0,75 mm | 13 300 |
| 7 × 7 = 49 | 0,64 mm | 18 240 |
| 8 × 8 = 64 | 0,56 mm | 23 940 |
| 9 × 9 = 81 | 0,50 mm | 30 400 |
| 10 × 10 = 100 | 0,45 mm | 37 620 |
| 11 × 11 = 121 | 0,40 mm | 45 600 |
| 12 × 12 = 144 | 0,37 mm | 54 340 |
| 13 × 13 = 169 | 0,34 mm | 63 840 |
| 14 × 14 = 196 | 0,32 mm | 74 100 |
| 15 × 15 = 225 | 0,30 mm | 85 120 |

Naturally, as a deviation from the table, non-square blocks can be used if this appears more favorable, for example positioning accuracy is not the same in the x and y direction.

The values on the table are all consistent with a position inaccuracy of 0.05 millimeters at a sample spot diameter of 0.20 millimeters. Naturally, the spot diameter could be selected much higher for 3×3 samples per block. At an average time of one minute for a loading cycle, the sample support for the samples from 11×11=121 microtiter plates is loaded in about two hours, for 15×15=225 microtiter plates in less than four hours. For a 96-tip multipipette, the loading times have to be multiplied by four.

It can happen that sensitive samples cannot be exposed to the air for long. This can become a problem during lengthy loading times. In this case it is possible to fill the entire loading apparatus with protective gas and then also transport the sample support plates covered in protective gas to the mass spectrometer. In the concurrent patent application DE 19 628 112, a cassette design is presented in which the sample support can be stored, transferred and fed into the mass spectrometer in protective gas.

Of course, the invention may also be applied analogously to other microtiter plates with other grid spacings.

Figure 1:
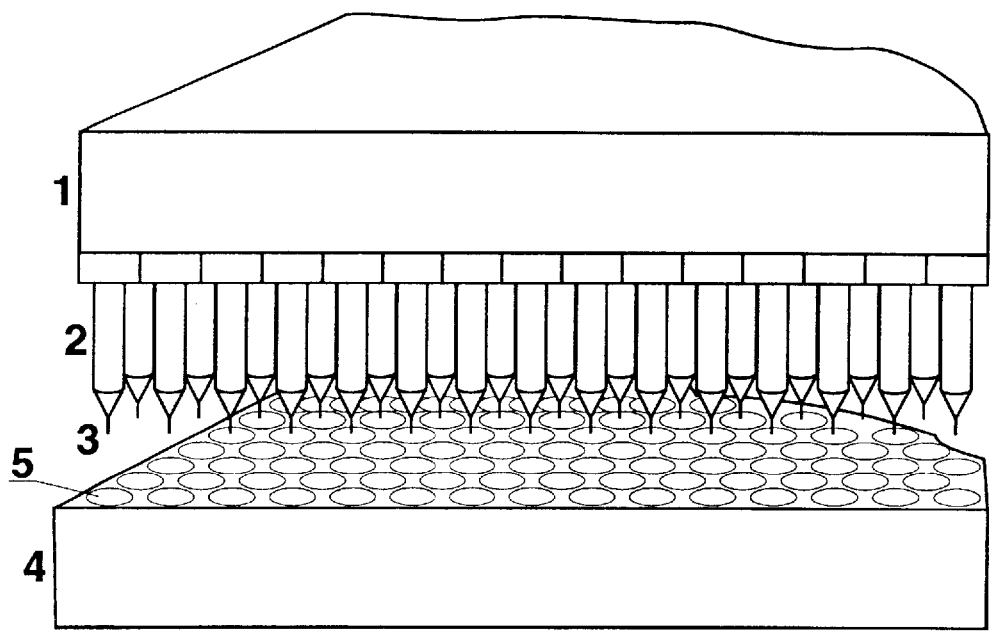
FIG. 1 shows a section of a multiple pipette unit (1) above a section from a microtiter plate (4). The individual pipettes have shafts (2) with conically pointed ends holding the pipette capillaries (3). The pipettes can be introduced into the recessed reaction wells (5) on the microtiter plate (4).

Therefore the position of all sample spots can be determined exactly by a measuring scan of one such block in the mass spectrometer, if only a parallel offset of the spots is to be expected. If an angular offset is also to be expected, two blocks must be measured. The block with the sample spots (7) in the corner of the sample support consists of reference substances which can easily be scanned for such position calibration. The white sample spots (9) are reference substances which allow an overall quality control. The black sample spots (8) are the unknown analysis samples.

Particularly favorable embodiments

The sample supports, according to this invention, conform precisely in their size to the microtiter plates. They can then be introduced and processed in commercially available processing stations for microtiter plates. These stations have become established in biochemistry for parallel processing of many samples; they are commercially available. The body size of these plates is 80 by 125 millimeters, with a usable surface of 72 by 108 millimeters, on which today usually 384 reaction wells (vials) are solidly recessed into the plastic in a 4.5 mm grid.

If microtiter plates with 864 reaction wells in a 3 mm grid are introduced in the future, these may also be used since they are the same size. Then the multipipette units and sample spot array for the sample blocks must be changed. Loading will then be faster since 864 samples each can be transferred at the same time.—If 96-tip multipipettes are used, these can readily handle 864-well microtiter plates, if only the shaft diameter is smaller than the well diameter. Nine sample transfer processes are then needed for each of the microtiter plates.

The invention is based upon the already introduced parallel processing of large numbers of samples in biochemistry and molecular genetics. The handling stations used here for the loading process are also being used for the preparation of the samples to be analyzed.

The sample supports in the size of microtiter plates must be provided with a MALDI layer. This can be done in the biochemical laboratory, however in the future it will preferably be done by industrial prepreparation. The MALDI layer may consist of a lacquer-like layer of nitrocellulose, for example, a suitable protonizing matrix component being added to the lacquer.

This lacquer layer is extraordinarily adsorptive for peptides, proteins and DNA. The molecules of the analysis substances are adsorbed very uniformly on the surface and thus allow automation of the MALDI ionization.

This layer must now be covered with the arrays of samples which were prepared in the microliter plates. Suitable for this are the well-known multiple pipette units. However, whereas to-day's multipipettes have only single rows of pipettes, here multipipettes with twodimensional arrays of pipettes are proposed, the individual pipettes of which are arranged in the grid pattern of the reaction wells of the microtiter plates.

The simplest embodiment of a multiple pipette unit consists of a plate into which pins have been screwed in the grid pattern of the reaction containers on the microtiter plates. In the conically pointed ends of the pins pipette wires have been inserted. The pipette wires project only slightly, about one or two millimeters, from the pin shaft, to prevent maladjustment. The wires are ground off in such a way that their ends are exactly in plane. When they dip into the reaction wells, filled to exactly the same height, on the microtiter plate, they are wetted in the same manner with sample solution, taking equal amounts of sample solution with them when they are lifted out. The diameter of the pipette wires determines the future size of the sample spot on the sample support.

The multiple pipette unit can also carry capillary pipettes, which have a design similar to microliter syringes. Using them, larger amounts of sample solution can be transferred.

The transfer to the sample support must be done very precisely. It can hardly be performed manually. Here the obvious solution is an automatic movement mechanism which can move the multiple pipette unit three-dimensionally with great accuracy. Such movement units can be constructed using linear motors, and they can run through paths of about one meter in length at speeds of about 20 meters per second with a positioning accuracy of 50 micrometers. The movement units may also have a robot hand besides the multiple pipette unit which can bring the microtiter plates from a magazine to a fixed intermediate station.

Using such a movement unit, the loading process of a sample support located in a support station can be performed using the following cycle according to this invention:

The robot hand picks up the first microtiter plate from a magazine, in which there are about 60 microtiter plates, and positions it precisely in the intermediate station. Each of the microtiter plates contains suitable reference samples of known concentration in the four comer wells. Then the multiple pipette unit is introduced into the reaction wells of the microtiter plate, whereby the pipette wires are wetted. The pipette unit is lifted out leaving solution droplets of about 200 micrometers diameter on the pipette wires. The pipette unit is then moved to the MALDI support plate station and after as accurate a positioning as possible, and after the remaining vibrations have ceased, it is lowered to about 50 micrometers above the sample support. The droplets then touch the MALDI layer on the sample support. During the subsequent lifting away of the pipette unit, the larger shares of the droplets remain on the MALDI layer, which then dry under the influence of dry, warm air within about 30 seconds.

The pipette unit is then moved to a washing station where it is cleaned in water which has been acidified with trifluoroacetic acid and in which there are also brushes to rub off residual sample material. The movement unit can move the pipette unit over the fixed brushes in a washing action. The second washing station consists of clean water. Then the pipettes are dried in a stream of warm, dry air.

In the next step, the robot hand returns the microtiter plate to the magazine and takes the next plate. The complete cycle lasts about 60 seconds. The cycle can be repeated as often as necessary until the sample support is completely loaded or the magazine with microtiter plates is empty. This must then be replaced with the next magazine.

Figure 2:
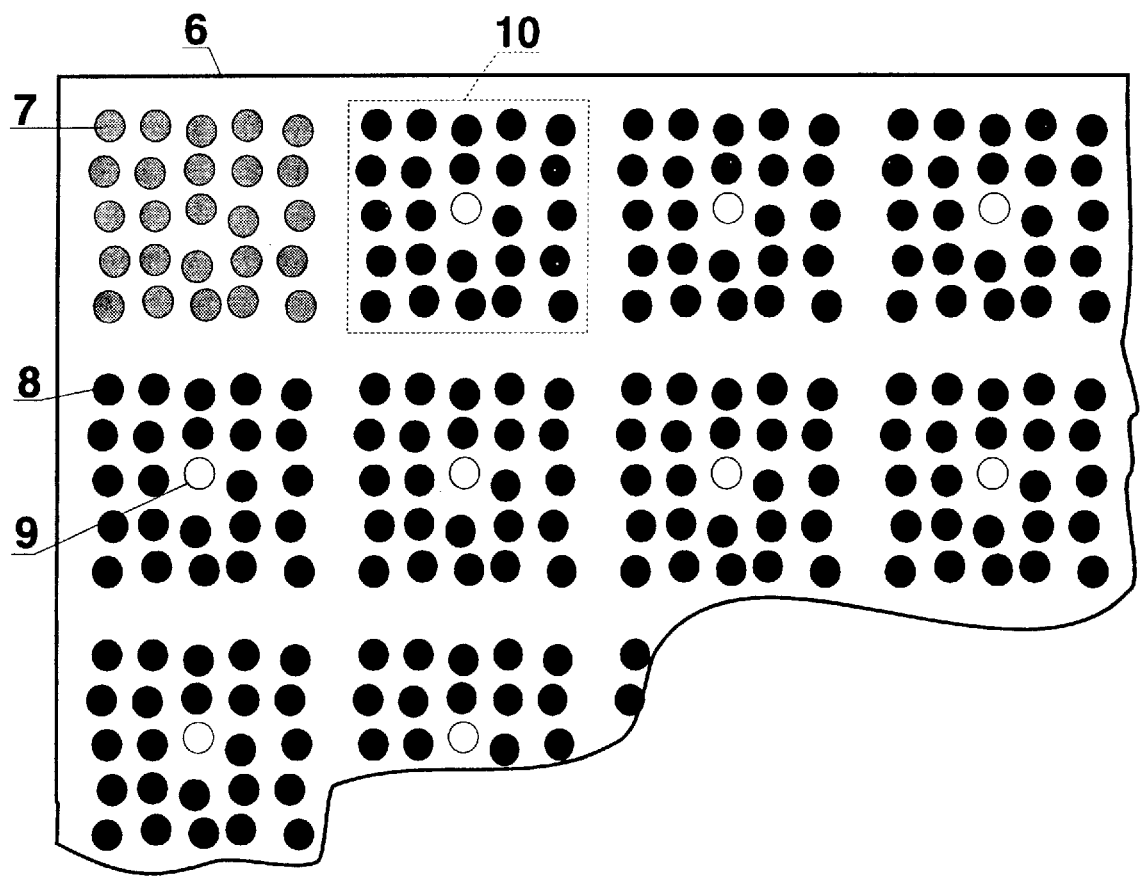
FIG. 2 shows a corner section of the sample support (6) after loading with samples. The sample spots are arranged in array blocks (10) of 5×5 sample spots each. The array blocks have a spacing from each other which corresponds to that of the reaction wells on the microtiter plate. The 25 samples in a sample array block (10) each originate from a different microtiter plate. The sample spots do not form an exactly positioned 5×5 array, since the positioning of the multiple pipette unit was not exactly accurate when applying the samples. The relative positioning within adjacent 5×5 blocks is nevertheless the same, due to the accuracy of the multipipette.

The point patterns must be applied slightly offset for each of the microtiter plates, so that the sample array blocks result as shown in FIG. 2. The blocks shown there with 24 analysis samples and a reference sample produce exactly 9,120 analyte samples applied in only 25 minutes on the basis of 380 reaction wells per microtiter plate. This may be enough for many purposes. For this number, replacement of the magazine is unnecessary, and loading can take place completely automatically. Even using a 96-tip multipipette instead of the 384-tip pipette, the loading process takes only about two hours.

If higher numbers of analyses are required, for example for medical screening analyses in searching for dangerous mutations, sample blocks with 11×11=121 sample spots can be applied. Here it is advisable, for increased safety, to apply the samples twice on different positions and again use one reference substance per block. Therefore samples from 60 microtiter plates with analytes and one microtiter plate with reference substance are taken, and again only one magazine is necessary, and the loading can take place again completely automatically without interruption. The loading for this takes about two hours.

Generally, the completely loaded sample supports must be treated further before analysis in a mass spectrometer. It is advisable to wash the sample supports in order to remove all salts and buffer substances from the surface. The molecules from the biochemical analysis substances are generally so firmly adsorbed that they are not removed during a careful washing procedure. It may also be necessary in borderline cases to remove all metal ions from the surface with special chemical or physical agents, because they sometimes tend to form adduct compounds. The carder plate must then be well dried so that not too much water is introduced into the mass spectrometer.

The sample supports are then introduced into the ion source of a suitable mass spectrometer and analyzed there. In the case of 11×11 sample spots, 22,800 samples must then be analyzed, a double measurement being undertaken for every sample. The total of 45,600 analyses can be performed in 25.3 hours if every analysis lasts exactly 2 seconds. Additional time is necessary for the position scanning and for analysis of the reference samples. To perform the analyses in somewhat less than one day, it is therefore practical to achieve analysis times below 2 seconds.

For easily degradable samples it may be necessary to carry out the entire loading process, for example, in an automatic device sealed with large glass panels under protective gas, e.g., nitrogen. Even the transportation of the ready loaded sample support plates to the mass spectrometer can be done under protective gas, using suitable cassettes.

The pipette tips can also be provided with suitable coatings which attract sample molecules for enrichment of the sample molecules. Also an electrophoretic enrichment can be applied. The attracted sample molecules can also be transferred using electrophoretic voltage to the MALDI layer.

I claim:

1. Method for rapidly loading of a large number of solved samples for mass spectrometric analysis from microtiter plates onto a sample support plate, comprising the steps
   (a) using a sample support plate in the size of a microtiter plate, and
   (b) transferring amounts of sample solution from microtiter plate wells to the sample support plate simultaneously for a large subset of the samples of the microtiter plate, using a multiple pipette.

2. Method according to claim 1, wherein the sample support plate is already covered with a matrix layer for matrix-assisted laser desorption and ionization (MALDI).

3. Method according to claim 1, wherein a multiple pipette with at least 96 pipette tips is used for the simultaneous transfer of the samples.

4. Method according to claim 3, wherein the multiple pipette has as many individual pipettes as the number of sample wells in the microtiter plate.

5. Method according to claim 3, wherein the multiple pipette consists of a large number of individual stamps, on each of which droplets of the dissolved sample remain hanging and can thus be transferred.

6. Method according to claim 5, wherein sample molecules are attracted and concentrated on the pipette tips using a electrophoresis voltage between the sample solution and the pipette tips, and wherein the sample molecules are transferred from the pipette tips to a MALDI layer by reversing the electrophoresis voltage.

7. Method according to claim 1, wherein the samples for a sample support are taken from several microtiter plates and sample spot arrays from different microtiter plates are interlaced.

8. Method according to claim 7, wherein the samples from different microtiter plates form blocks of sample spots on the sample support plate, and one such block is smaller than the area on the microtiter plate belonging to one reaction well.

9. Method according to claim 8, wherein the samples from 4 microtiter plates with 384 sample wells each are applied in blocks of 2×2 sample spots with a spacing of about 2 millimeters, so that there are 1,536 sample spots on the sample support plate after loading.

10. Method according to claim 8, wherein the samples from 25 microtiter plates with 384 sample wells each are applied in blocks of 5×5 sample spots with a spacing of 0.9 millimeters, so that there are 9,600 sample spots on the sample support plate after loading.

11. Method according to claim 8, wherein the samples from 121 microtiter plates with 384 sample wells each are applied in blocks of 11×11 sample spots with a spacing of 0.4 millimeters, so that there are 46,464 sample spots on the sample support plate after loading.

12. Method according to claim 8, wherein at least one block of samples is used to determine the exact positions of the sample spots relative to the other samples of the block and relative to the sample support plate area after the sample support has been inserted into the mass spectrometer.

13. Method according to claim 12, wherein the four blocks for this determination of the relative positions are located in the corners of the sample support plate.

14. Method according to claim 8, wherein one sample spot each from the blocks consists of a known substance for the purposes of analytical quality assurance.

15. Method according to claim 7, wherein every sample from every microtiter plate is applied by double transfer of the samples from each microtiter plate twice at different positions for purposes of quality assurance using double measurements.

* * * * *